United States Patent
Jaouani et al.

(10) Patent No.: US 11,497,941 B2
(45) Date of Patent: *Nov. 15, 2022

(54) COSMETIC COMPOSITION COMPRISING AN ORGANOSILANE, A CATIONIC SURFACTANT AND A CATIONIC POLYMER HAVING CHARGE DENSITY GREATER THAN OR EQUAL TO 4 MEQ/G

(71) Applicant: L'OREAL, Paris (FR)

(72) Inventors: Karima Jaouani, Gennevilliers (FR); Nicolas Daubresse, La Celle Saint-cloud (FR); Estelle Mathonneau, Paris (FR); Audrey Correia, Clichy (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/529,266

(22) PCT Filed: Nov. 27, 2015

(86) PCT No.: PCT/EP2015/077927

§ 371 (c)(1),
(2) Date: May 24, 2017

(87) PCT Pub. No.: WO2016/083578

PCT Pub. Date: Jun. 2, 2016

(65) Prior Publication Data

US 2017/0259087 A1 Sep. 14, 2017

(30) Foreign Application Priority Data

Nov. 27, 2014 (FR) ...................................... 1461567

(51) Int. Cl.
| | | |
|---|---|---|
| A61Q 5/12 | (2006.01) | |
| A61K 8/41 | (2006.01) | |
| A61K 8/58 | (2006.01) | |
| A61K 8/81 | (2006.01) | |
| A61Q 5/02 | (2006.01) | |
| A61K 47/14 | (2017.01) | |

(52) U.S. Cl.
CPC ............... *A61Q 5/12* (2013.01); *A61K 8/416* (2013.01); *A61K 8/585* (2013.01); *A61K 8/817* (2013.01); *A61K 47/14* (2013.01); *A61Q 5/02* (2013.01); *A61K 2800/5426* (2013.01)

(58) Field of Classification Search
CPC ............ A61Q 5/12; A61Q 5/02; A61K 47/14; A61K 8/416; A61K 8/585; A61K 8/817; A61K 2800/5426
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,206,462 A | 9/1965 | McCarty |
| 3,227,615 A | 1/1966 | Korden |
| 3,632,559 A | 1/1972 | Matter et al. |
| 3,874,870 A | 4/1975 | Green et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,075,136 A | 2/1978 | Schaper |
| 4,137,180 A | 1/1979 | Naik et al. |
| 4,172,887 A | 10/1979 | Vanlerberghe et al. |
| 4,197,865 A | 4/1980 | Jacquet et al. |

(Continued)

FOREIGN PATENT DOCUMENTS

| | | |
|---|---|---|
| EP | 0159628 A2 | 10/1985 |
| EP | 0337354 A1 | 10/1989 |

(Continued)

OTHER PUBLICATIONS

International Search Report for Application No. PCT/2015/077927, dated Mar. 1, 2016.
Mintel, "Hair Conditioner," XP002742867, Dec. 2013.
Mintel, "Masque for Fine Hair," XP002742866, Jun. 2011.
Todd, Charles, et al., "Volatile Silicone Fluids for Cosmetic Formulations," Cosmetics and Toiletries, vol. 91, Jan. 1976, pp. 29-32.
International Search Report for counterpart Application No. PCT/EP2016/081023, dated Feb. 24, 2017.
Non-Final Office Action for co-pending U.S. Appl. No. 16/061,858, dated Apr. 5, 2019.
Non-Final Office Action for co-pending U.S. Appl. No. 16/061,858, dated Oct. 31, 2019.
Final Office Action for copending U.S. Appl. No. 16/061,858, dated Jun. 12, 2020.

*Primary Examiner* — Abigail Vanhorn
(74) *Attorney, Agent, or Firm* — The Marbury Law Group, PLLC

(57) ABSTRACT

The present invention relates to a cosmetic composition for the treatment of keratin fibres, particularly human keratin fibres such as hair, comprising, in a cosmetically acceptable medium, one or more organosilanes, one or more cationic polymers having charge density greater than or equal to 4 meq/g and one or more cationic surfactants. The present invention also relates to a cosmetic process for treating keratin fibres using said cosmetic composition. The present invention finally relates to the use of said composition for the cosmetic treatment of keratin fibres.

7 Claims, No Drawings

(56) References Cited

U.S. PATENT DOCUMENTS

| | | |
|---|---|---|
| 4,217,914 A | 8/1980 | Jacquet et al. |
| 4,240,450 A | 12/1980 | Grollier et al. |
| 4,349,532 A | 9/1982 | Vanlerberghe et al. |
| 4,591,610 A | 5/1986 | Grollier |
| 4,761,273 A | 8/1988 | Grollier et al. |
| 4,839,166 A | 6/1989 | Grollier et al. |
| 4,874,554 A | 10/1989 | Lange et al. |
| 4,996,059 A | 2/1991 | Grollier et al. |
| 5,089,252 A | 2/1992 | Grollier et al. |
| 6,159,914 A | 12/2000 | DeCoster et al. |
| 6,451,747 B1 | 9/2002 | Decoster |
| 9,248,083 B2 | 2/2016 | Aires et al. |
| 10,071,048 B2 * | 9/2018 | Sturla .................... A61K 8/817 |
| 2006/0110351 A1 | 5/2006 | Koehler et al. |
| 2007/0060489 A1 | 3/2007 | Sun et al. |
| 2009/0291058 A1 | 11/2009 | Woodland et al. |
| 2011/0158927 A1 | 6/2011 | Viravau et al. |
| 2012/0328542 A1 | 12/2012 | Samain et al. |
| 2013/0233331 A1 | 9/2013 | Khenniche et al. |
| 2013/0251656 A1 | 9/2013 | Khenniche et al. |
| 2014/0314696 A1 | 10/2014 | Kergosien et al. |
| 2015/0047664 A1 | 2/2015 | Samain et al. |
| 2018/0369109 A1 * | 12/2018 | Mathonneau ......... A61K 8/416 |

FOREIGN PATENT DOCUMENTS

| | | | |
|---|---|---|---|
| EP | 1736139 A1 | 12/2006 | |
| EP | 2111848 A2 | 10/2009 | |
| EP | 2343042 A2 | 7/2011 | |
| EP | 2471506 A1 | 7/2012 | |
| FR | 1583363 A | 10/1969 | |
| FR | 2080759 A1 | 11/1971 | |
| FR | 2162025 A | 7/1973 | |
| FR | 2190406 A2 | 2/1974 | |
| FR | 2252840 A1 | 6/1975 | |
| FR | 2270846 A1 | 12/1975 | |
| FR | 2280361 A2 | 2/1976 | |
| FR | 2316271 A1 | 1/1977 | |
| FR | 2320330 A1 | 3/1977 | |
| FR | 2336434 A1 | 7/1977 | |
| FR | 2368508 A2 | 5/1978 | |
| FR | 2383660 A1 | 10/1978 | |
| FR | 2413907 A1 | 8/1979 | |
| FR | 2470596 A1 | 6/1981 | |
| FR | 2505348 A1 | 11/1982 | |
| FR | 2519863 A1 | 7/1983 | |
| FR | 2542997 A1 | 9/1984 | |
| FR | 2598611 A1 | 11/1987 | |
| FR | 2910276 A1 | 6/2008 | |
| FR | 2930438 A1 | 10/2009 | |
| FR | 2954099 A1 | 6/2011 | |
| FR | 2954100 A1 | 6/2011 | |
| FR | 2954129 A1 | 6/2011 | |
| FR | 2966350 A1 | 4/2012 | |
| FR | 2966351 A1 | 4/2012 | |
| FR | 2966352 A1 | 4/2012 | |
| FR | 2999077 A1 | 6/2014 | |
| GB | 1546809 A | 5/1979 | |
| JP | 2002-356672 A | 12/2002 | |
| RU | 2150265 C1 | 6/2000 | |
| RU | 2177779 C2 | 1/2002 | |
| RU | 2007134258 A | 3/2009 | |
| WO | 2004/012691 A1 | 2/2004 | |
| WO | 2009/011677 A1 | 1/2009 | |
| WO | 2012/055805 A1 | 5/2012 | |
| WO | WO-2012163869 A2 * | 12/2012 | ............ A61K 8/585 |
| WO | 2013/144871 A1 | 10/2013 | |
| WO | WO-2014124066 A1 * | 8/2014 | ............... A61K 8/27 |

* cited by examiner

COSMETIC COMPOSITION COMPRISING AN ORGANOSILANE, A CATIONIC SURFACTANT AND A CATIONIC POLYMER HAVING CHARGE DENSITY GREATER THAN OR EQUAL TO 4 MEQ/G

CROSS REFERENCE TO RELATED APPLICATIONS

This is a national stage application of PCT/EP2015/077927, filed internationally on Nov. 27, 2015, which claims priority to French Application No. 1461567, filed on Nov. 27, 2014, both of which are incorporated by reference herein in their entireties.

The present invention relates to a cosmetic composition for the treatment of keratin fibres, particularly human keratin fibres such as hair, comprising, in a cosmetically acceptable medium, one or more organosilanes, one or more cationic polymers having charge density greater than or equal to 4 meq/g and one or more cationic surfactants.

The present invention also relates to a cosmetic process for treating keratin fibres using said cosmetic composition.

The present invention finally relates to the use of said composition for the cosmetic treatment of keratin fibres.

Hair is generally damaged and embrittled by the action of external atmospheric agents such as light and bad weather, and by mechanical or chemical treatments, such as brushing, combing, dyeing, bleaching, permanent-waving and/or relaxing.

Accordingly, to remedy these drawbacks, it is now usual to pursue hair care treatments involving the use of care compositions that condition hair after these treatments to give them in particular shine, softness, suppleness, lightness, a natural feel and detangling properties.

These haircare compositions may be, for example, conditioning shampoos or compositions to be applied before or after washing with shampoo, and may be in the form of gels, hair lotions or creams of varying thickness.

It is known, in order to improve the cosmetic properties of these compositions, to introduce therein cosmetic agents, known as conditioning agents, intended mainly to repair or to limit the harmful or undesirable effects brought about by the various treatments or attacks to which hair fibres are more or less repeatedly subjected.

With this goal, using organosilicon compounds (organosilanes) in cosmetic care compositions, among others, to give hair satisfactory conditioning properties has already been proposed.

Such compositions are for example described in patent applications FR 2910276, EP 2343042 and EP 2111848.

However, the care compositions described in the prior art secure conditioning and detangling properties that do not last sufficiently long. Indeed, these properties do not generally resist washing sufficiently and tend to diminish from the first wash with shampoo.

Moreover, compositions comprising organosilicon compounds often exhibit the disadvantage of changing substantially over time under normal storage conditions, in particular as regards their viscosity and their visual appearance.

This means that their visual appearance may become cloudy and/or they may have a less satisfactory texture, which can reduce the efficacy of these compositions.

Accordingly, a real need exists to make available a cosmetic care composition for keratin fibres, particularly human keratin fibres such as hair, that do not have the drawbacks mentioned above, i.e. that is in particular capable of securing conditioning properties not only satisfactory but also long-lasting upon washing, for example long-lasting for at least 3 washes with shampoo. These compositions must also remain stable over time.

The Applicant has discovered, in a surprising manner, that a composition comprising one or more organosilicon compounds as defined hereinafter, one or more cationic polymers having charge density greater than or equal to 4 meq/g and one or more cationic surfactants, could allow the objectives set out above to be reached.

Therefore the present invention relates to a cosmetic composition for caring for keratin fibres, particularly human keratin fibres such as hair, comprising in a cosmetically acceptable medium:
(i) one or more organosilanes chosen from compounds having formula (I) and/or oligomers thereof:

$$R_1Si(OR_2)_z(R_3)_x(OH)_y$$ (I)

in which
$R_1$ is a cyclic or acyclic, linear or branched, saturated or unsaturated $C_1$ to $C_{22}$, in particular $C_2$ to $C_{20}$, hydrocarbon-based chain, which may be substituted with a group chosen from amine groups $NH_2$ or NHR (R being a linear or branched $C_1$ to $C_{20}$, in particular $C_1$ to $C_6$, alkyl, a $C_3$ to $C_{40}$ cycloalkyl or a $C_6$ to $C_{30}$ aromatic radical); the hydroxyl group (OH), a thiol group, an aryl group (more particularly benzyl), which is possibly substituted with an $NH_2$ or NHR group; it being possible for $R_1$ to be interrupted with a heteroatom (O, S or NH) or a carbonyl group (CO), $R_2$ and $R_3$, which are identical or different, represent a linear or branched alkyl group comprising from 1 to 6 carbon atoms, y denotes an integer ranging from 0 to 3,
z denotes an integer ranging from 0 to 3, and
x denotes an integer ranging from 0 to 2,
with z+x+y=3
(ii) one or more cationic polymers having charge density greater than or equal to 4 meq/g, and
(iii) one or more cationic surfactants.

The present invention also relates to a method for the cosmetic treatment of keratin fibres in which the composition according to the invention is applied to said fibres.

The present invention also relates to the use of said composition to give hair a cosmetic treatment that is long-lasting after being washed with shampoo.

The composition according to the invention secures a particularly satisfactory coating for hair, and in particular gives it softness, suppleness, smoothness, lightness, volume, and a natural non-greasy, lightweight feel. This composition also provides hair with improved detangling ability.

Moreover, the properties secured by the composition according to the invention resist the diverse attacks that hair may undergo well, such as light, bad weather, washing, perspiration. They are particularly long-lasting when washed with shampoo, in particular for at least 3 washes.

The composition according to the invention is further stable over time.

"Stable" within the meaning of the present invention is understood to mean that the visual appearance and the viscosity of these compositions do not change or do not substantially change (variation generally of less than 10%, with respect to the viscosity at T0) over time under standard storage conditions, for example over the month or the two months which follow their manufacture, at ambient temperature.

Other subjects, characteristics, aspects and advantages of the invention will emerge even more clearly on reading the description and the examples that follow.

In that which follows and unless otherwise indicated, the limits of a range of values are included within this range, in particular in the expressions "of between" and "ranging from . . . to . . . ".

Moreover, the expressions "at least one" and "at least" used in this description are equivalent to the expressions "one or more" and "greater than or equal" respectively.

Organosilanes

The composition according to the invention comprises one or more organosilanes chosen from compounds having formula (I) and/or oligomers thereof:

$$R_1Si(OR_2)_z(R_3)_x(OH)_y \qquad (I)$$

in which $R_1$ is a cyclic or acyclic, linear or branched, saturated or unsaturated $C_1$ to $C_{22}$, in particular $C_2$ to $C_{20}$, hydrocarbon-based chain, which may be substituted with a group chosen from amine groups $NH_2$ or NHR (R being a linear or branched $C_1$ to $C_{20}$, in particular $C_1$ to $C_6$, alkyl, a $C_3$ to $C_{40}$ cycloalkyl or a $C_6$ to $C_{30}$ aromatic radical); the hydroxyl group (OH), a thiol group, an aryl group (more particularly benzyl), which is possibly substituted with an $NH_2$ or NHR group; it being possible for $R_1$ to be interrupted with a heteroatom (O, S or NH) or a carbonyl group (CO), $R_2$ and $R_3$, which are identical or different, represent a linear or branched alkyl group comprising from 1 to 6 carbon atoms, y denotes an integer ranging from 0 to 3,
z denotes an integer ranging from 0 to 3, and
x denotes an integer ranging from 0 to 2,
with z+x+y=3.

The term "oligomer" is intended to mean the polymerization products of the compounds having formula (I) including from 2 to 10 silicon atoms.

Preferably, $R_1$ is a linear or branched, preferably linear, saturated $C_1$ to $C_{22}$, in particular $C_2$ to $C_{12}$, hydrocarbon-based chain, which may be substituted with an amine group $NH_2$ or NHR (R=$C_1$ to $C_{20}$, in particular $C_1$ to $C_6$, alkyl).

Preferably, $R_2$ represents an alkyl group comprising from 1 to 4 carbon atoms, better still a linear alkyl group comprising from 1 to 4 carbon atoms, and preferably the ethyl group.

Preferably, z ranges from 1 to 3.
Preferably, y=0.
Preferentially, z=3, and therefore x=y=0.

In one embodiment of the invention, the organosilane(s) are chosen from among compounds having formula (I) in which $R_1$ represents a linear alkyl group comprising from 7 to 18 carbon atoms and more particularly from 7 to 12 carbon atoms, or a $C_1$ to $C_6$, preferably $C_2$ to $C_4$, aminoalkyl group. More particularly, $R_1$ represents an octyl group.

In another embodiment of the invention, the organosilane(s) are chosen from compounds having formula (I) in which $R_1$ is a linear or branched, saturated or unsaturated $C_1$ to $C_{22}$ hydrocarbon-based chain, substituted by an $NH_2$ or NHR amine group (with R=$C_1$ to $C_{20}$ alkyl, in particular $C_1$ to $C_6$, $C_3$ to $C_{40}$ cycloalkyl or $C_6$ to $C_{30}$ aromatic). In this variant, $R_1$ preferably represents a $C_1$ to $C_6$, and more preferably $C_2$ to $C_4$, aminoalkyl group.

Preferably, the composition according to the invention comprises one or more organosilanes having formula (I) chosen from octyltriethoxysilane (OTES), dodecyltriethoxysilane, octadecyltriethoxysilane, hexadecyltriethoxysilane, 3-aminopropyltriethoxysilane (APTES), 2-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane, N-(2-aminoethylaminomethyl)phenethyltrimethoxysilane, and oligomers and mixtures thereof; and more particularly chosen from octyltriethoxysilane (OTES) and 3-aminopropyltriethoxysilane (APTES), and oligomers and mixtures thereof.

The organosilanes having formula (I) used in the composition of the invention, in particular those including a basic function, may be partially or totally neutralised in order to improve the water-solubility thereof. In particular, the neutralising agent may be chosen from organic or inorganic acids, such as citric acid, tartaric acid, lactic acid or hydrochloric acid.

Preferably, the optionally neutralised organosilanes having formula (I) according to the invention are water-soluble and in particular soluble at a concentration of 2% by weight, better still at a concentration of 5% by weight and even better still at a concentration of 10% by weight in water at a temperature of 25° C. and at atmospheric pressure (1 atm). The term "soluble" is intended to mean the formation of a single macroscopic phase.

The organosilane(s) having formula (I) may be present in the composition according to the invention in a content ranging from 0.1% to 15% by weight, preferably ranging from 1% to 10% by weight and more preferably ranging from 2% to 8% by weight relative to the total weight of the composition.

Cationic Polymers

The composition according to the invention further comprises one or more cationic polymers having charge density greater than or equal to 4 meq/g (milliequivalents per gram).

More preferably still, the cationic charge density is greater than or equal to 5 meq/g, and more preferably may vary from 5 to 20 meq/g.

The cationic charge density of a polymer corresponds to the number of moles of cationic charges per unit mass of polymer under conditions in which it is totally ionized. It may be determined by calculation if the structure of the polymer is known, i.e. the structure of the monomers constituting the polymer and their molar proportion or weight proportion. It may also be determined experimentally by the Kjeldahl method.

The cationic polymers having a cationic charge density of greater than or equal to 4 meq/g that may be used in accordance with the present invention may be chosen from all those already known per se as improving the cosmetic properties of hair treated with detergent compositions, i.e. especially those described in patent application EP-A-0 337 354 and in French patent applications FR-A-2 270 846, 2 383 660, 2 598 611, 2 470 596 and 2 519 863.

In general, for the purposes of the present invention, the term "cationic polymer" denotes any polymer comprising cationic groups and/or groups that may be ionized into cationic groups.

The cationic polymers used in the present invention preferably have an average molecular weight by number greater than or equal to 50 000 g/mol, and more preferentially, greater than or equal to 100 000 g/mol.

The cationic polymers used according to the present invention are advantageously chosen from those that contain units including primary, secondary, tertiary and/or quaternary amine groups that may either form part of the main polymer chain or may be carried by a side substituent directly connected thereto.

More particularly, the cationic polymers present in the composition according to the present invention are chosen from polymers from the types polyamine, polyaminoamide and quaternary polyammonium, polyalkyleneimines and mixtures thereof.

The polymers of polyamine, polyamidoamide and polyquaternary ammonium type that can be used in accordance with the present invention, and that can in particular be mentioned, are those described in French patents No. 2 505 348 or 2 542 997. Among these polymers, mention may be made of:

(1) Quaternized or non-quaternized vinylpyrrolidone/dialkylaminoalkyl (meth)acrylate copolymers.

(2) Polymers composed of piperazinyl units and of divalent alkylene or hydroxyalkylene groups containing straight or branched chains, optionally interrupted by oxygen, sulfur or nitrogen atoms or by aromatic or heterocyclic rings, and also the oxidation and/or quaternization products of these polymers. Such polymers are described, in particular, in French patents 2162025 and 2280361;

(3) water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they include one or more tertiary amine functions, they can be quaternized. Such polymers are in particular described in French patents 2 252 840 and 2 368 508.

(4) Polyaminoamide derivatives resulting from the condensation of polyalkylene-polyamines with polycarboxylic acids, followed by alkylation with difunctional agents. Mention may be made, for example, of adipic acid/dialkylaminohydroxyalkyldialkylenetriamine polymers in which the alkyl group includes from 1 to 4 carbon atoms and preferably denotes methyl, ethyl or propyl. Such polymers are in particular described in French patent 1583363.

(5) polymers obtained by reaction of a polyalkylene polyamine containing two primary amine groups and at least one secondary amine group with a dicarboxylic acid chosen from diglycolic acid and saturated aliphatic dicarboxylic acids containing from 3 to 8 carbon atoms. The molar ratio between the polyalkylene-polyamine and the dicarboxylic acid is between 0.8:1 and 1.4:1; the resulting polyaminoamide is reacted with epichlorohydrin in a mole ratio of epichlorohydrin relative to the secondary amine group of the polyaminoamide of between 0.5:1 and 1.8:1. Such polymers are described in particular in U.S. Pat. Nos. 3,227,615 and 2,961,347.

(6) alkyldiallylamine or dialkyldiallylammonium cyclopolymers, such as homopolymers or copolymers including units corresponding to the formulae (IV) or (V):

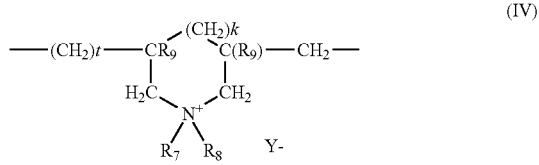

(IV)

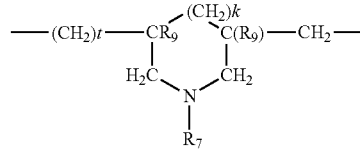

(V)

in which, k and t are equal to 0 or 1, the sum k+t being equal to 1;

$R_9$ denotes a hydrogen atom or a methyl group;

$R_7$ and $R_8$, independently of each other, denote an alkyl group having from 1 to 22 carbon atoms, a hydroxyalkyl group in which the alkyl group contains preferably 1 to 5 carbon atoms, a lower amidoalkyl group; or alternatively $R_7$ and $R_8$ may denote, together with the nitrogen atom to which they are attached, heterocyclic groups such as piperidyl or morpholinyl; and $Y^-$ is an anion such as bromide, chloride, acetate, borate, citrate, tartrate, bisulfate, bisulfite, sulfate or phosphate;

Such polymers are especially described in French patent 2080759 and its certificate of addition 2190406.

Mention may be made, for example, of the diallyldimethylammonium chloride homopolymer sold under the name "MERQUAT® 100" by the company NALCO (LUBRIZOL), and the diallyldimethylammonium chloride-acrylamide copolymers.

(7) diquaternary ammonium polycondensates containing repeating units corresponding to the formula (VI):

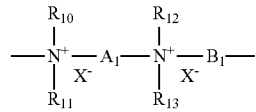

(VI)

in which, $R_{10}$, $R_{11}$, $R_{12}$ and $R_{13}$, which may be identical or different, represent aliphatic, alicyclic or arylaliphatic groups containing from 1 to 20 carbon atoms or lower hydroxyalkylaliphatic groups, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ represent a linear or branched $C_1$ to $C_6$ alkyl group substituted with a nitrile, ester, acyl or amide group or a group —CO—O—R-D or —CO—NH—R-D where R is an alkylene group and D is a quaternary ammonium group, $A_1$ and $B_1$ represent polymethylene groups containing from 2 to 20 carbon atoms, which may be linear or branched, and saturated or unsaturated, and which may contain, linked to or inserted in the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene group, $B_1$ can also denote a —(CH$_2$)n-CO-D-OC—(CH$_2$)n- group, in which D denotes:

a) a glycol residue having formula: —O—Z—O—, where Z denotes a linear or branched hydrocarbon-based group or a group corresponding to one of the following formulae:

—(CH$_2$—CH$_2$—O)$x$-CH$_2$—CH$_2$—

—[CH$_2$—CH(CH$_3$)—O]$_y$—CH$_2$—CH(CH$_3$)— where x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue having formula: —NH—Y—NH—, where Y denotes a linear or branched hydrocarbon group, or alternatively the divalent group

—CH$_2$—CH$_2$—S—S—CH$_2$—CH$_2$—;

d) a ureylene group having formula: —NH—CO—NH—.

Preferably, X$^-$ is an anion such as chloride or bromide.

These polymers have a number-average molecular mass generally between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may more particularly be made of polymers that are formed from repeating units corresponding to formula (VII):

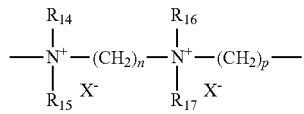

(VII)

in which, $R_{14}$, $R_{15}$, $R_{16}$ and $R_{17}$, which may be identical or different, each denote an alkyl or hydroxyalkyl group containing from 1 to 4 carbon atoms approximately, n and p are integers ranging from 2 to 20 approximately, and X$^-$ denotes an anion derived from an inorganic or organic acid.

A compound having formula (VII) that is particularly preferred is the one for which $R_{14}$, $R_{15}$, $R_{16}$ and $R_{17}$ represent a methyl group and n=3, p=6 and X=Cl, which is known as hexadimethrine chloride according to the INCI (CTFA) nomenclature.

(8) polyquaternary ammonium polycondensates composed of units having formula (VIII):

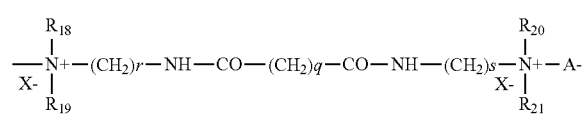

(VIII)

in which, $R_{18}$, $R_{19}$, $R_{20}$ and $R_{21}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH group, where p is equal to 0 or to an integer of between 1 and 6, with the proviso that $R_{18}$, $R_{19}$, $R_{20}$ and $R_{21}$ do not simultaneously represent a hydrogen atom, r and s, which may be identical or different, are integers between 1 and 6, q is equal to 0 or to an integer between 1 and 34, X denotes a halogen atom, and A denotes a dihalide group or represents preferably —CH$_2$—CH$_2$—O—CH$_2$—CH$_2$—.

Such compounds are described especially in patent application EP-A-122 324.

Mention may be made among these, for example, of the Miranol® A 15, Miranol® AD1, Miranol® AZ1 and Miranol® 175 products sold by the company Miranol.

(9) homopolymers or copolymers derived from acrylic or methacrylic acids and including units (IX), (X) and/or (XI):

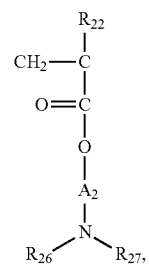

(IX)

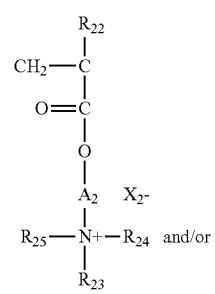

(X)

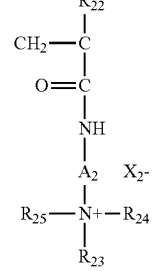

(XI)

in which, $R_{22}$ independently denotes H or CH$_3$, $A_2$ independently denotes a linear or branched alkyl group having 1 to 6 carbon atoms or a hydroxyalkyl group having 1 to 4 carbon atoms, $R_{23}$, $R_{24}$, $R_{25}$, which may be identical or different, independently denote an alkyl group having 1 to 18 carbon atoms or a benzyl group, $R_{26}$ and $R_{27}$ represent a hydrogen atom or an alkyl group having 1 to 6 carbon atoms, and $X_2^-$ denotes an anion, for example methosulfate or halide, such as chloride or bromide.

The comonomer(s) that can be used in preparing corresponding copolymers belong to the family of acrylamides, methacrylamides, diacetoneacrylamides, acrylamides and methacrylamides substituted on the nitrogen by lower alkyls, alkyl esters, acrylic or methacrylic acids, vinylpyrrolidone or vinyl esters.

(10) Quaternary polymers of vinylpyrrolidone and of vinylimidazole.

(11) Crosslinked polymers of methacryloyloxy($C_1$-$C_4$) alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, in particular methylenebisacrylamide.

Other cationic polymers that may be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among all the cationic polymers having charge density greater than or equal to 4 meq/g that can be used in the scope of the present invention, those preferred are chosen from families (6), (7), (9) and (11), as defined hereinbefore, and more preferentially chosen from:

crosslinked polymers of methacryloyloxyalkyl($C_1$-$C_4$) trialkyl($C_1$-$C_4$)ammonium salts, alkyldiallylamine or dialkyldiallylammonium cyclopolymers, homopolymers or copolymers derived from acrylic or methacrylic acids and including units (IX), as defined hereinabove, and mixtures thereof.

Preferably, the cationic polymer(s) having charge density greater than or equal to 4 meq/g, present in the composition according to the invention are chosen from 2-methacryloyloxyethyl trimethylammonium chloride (Polyquaternium-37), dimethyldiallyl ammonium chloride (Polyquaternium-6) and their mixtures.

The cationic polymers having charge density greater than or equal to 4 meq/g may be present in the composition according to the invention in a content ranging from 0.01% to 15% by weight, preferably ranging from 0.05% to 10% by weight and more preferably ranging from 0.1% to 5% by weight relative to the total weight of the composition.

Cationic Surfactants

The composition according to the invention can additionally include one or more cationic polymers.

The term "cationic surfactant" means a surfactant that is positively charged when it is contained in the composition according to the invention. This surfactant can carry one or more permanent positive charges or can contain one or more functional groups which can be converted to cations within the composition according to the invention.

The cationic surfactant(s) are preferably chosen from primary, secondary or tertiary fatty amines, which are optionally polyoxyalkylenated, or their salts, and quaternary ammonium salts, and their mixtures.

The fatty amines generally comprise at least one $C_8$ to $C_{30}$ hydrocarbon chain.

Examples of quaternary ammonium salts that may especially be mentioned include:

(a) those corresponding to the general formula (XII) below:

in which, $R_{28}$ to $R_{31}$ groups, which can be identical or different, represent a linear or branched aliphatic group including from 1 to 30 carbon atoms or an aromatic group, such as aryl or alkylaryl, at least one of the $R_{28}$ to $R_{31}$ groups denoting a group including from 8 to 30 carbon atoms, preferably from 12 to 24 carbon atoms. The aliphatic groups may include heteroatoms such as, in particular, oxygen, nitrogen, sulfur and halogens. The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate, and $C_1$-$C_{30}$ hydroxyalkyl groups, $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts having formula (XII), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salt, the stearamidopropyltrimethylammonium salt, the stearamidopropyldimethylcetearylammonium salt, or the stearamidopropyldimethyl(myristyl acetate)ammonium salt sold under the name Ceraphyl® 70 by the company Van Dyk. It is particularly preferred to use the chloride salts of these compounds.

(b) quaternary ammonium imidazoline salts, such as, for example, those having formula (VIII) below:

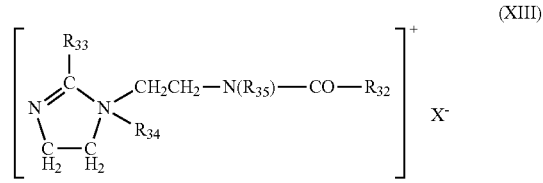

in which, $R_{32}$ represents an alkenyl or alkyl group including from 8 to 30 carbon atoms, for example fatty acid derivatives of tallow, $R_{33}$ represents a hydrogen atom, a $C_1$ to $C_4$ alkyl group or an alkenyl or alkyl group including from 8 to 30 carbon atoms;

$R_{34}$ represents a $C_1$ to $C_4$ alkyl group, $R_{35}$ represents a hydrogen atom or a $C_1$ to $C_4$ alkyl group, and X⁻ is an anion chosen from the group of halides, phosphates, acetates, lactates, alkyl sulfates, alkyl- or alkylarylsulfonates in which the alkyl and aryl groups preferably comprise, respectively, from 1 to 20 carbon atoms and from 6 to 30 carbon atoms.

Preferably, $R_{32}$ and $R_{33}$ denote a mixture of alkenyl or alkyl groups including from 12 to 21 carbon atoms, for example derived from tallow fatty acids, $R_{34}$ denotes a methyl group and $R_{35}$ denotes a hydrogen atom. Such a product is sold, for example, under the name Rewoquat® W 75 by Rewo;

(c) quaternary di- or triammonium salts in particular having formula (XIV):

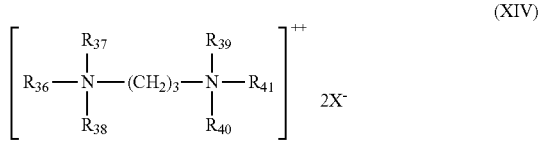

(XIV)

in which,
$R_{36}$ denotes an alkyl group including approximately from 16 to 30 carbon atoms, which is optionally hydroxylated and/or interrupted with one or more oxygen atoms;
$R_{37}$ is chosen from hydrogen or an alkyl group including 1 to 4 carbon atoms or a $(R_{36a})(R_{37a})(R_{38a})N$—$(CH_2)_3$, $R_{36a}$, $R_{37a}$, $R_{38a}$, $R_{38}$, $R_{39}$, $R_{40}$ and $R_{41}$ group, which may be identical or different, are chosen from hydrogen or an alkyl group including 1 to 4 carbon atoms, and
X⁻ is an anion chosen from the group of halides, acetates, phosphates, nitrates and methyl sulfates.

Such compounds are, for example, Finquat CT-P, sold by the company Finetex (Quaternium 89), and Finquat CT, sold by the company Finetex (Quaternium 75);

(d) quaternary ammonium salts containing at least one ester function, such as those having formula (XV) below:

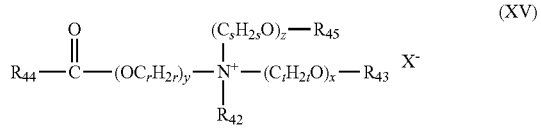

(XV)

in which:
$R_{42}$ is chosen from $C_1$ to $C_6$ alkyl groups and $C_1$ to $C_6$ hydroxyalkyl or dihydroxyalkyl groups;
$R_{43}$ is chosen from:
  the group

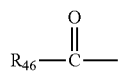

$R_{47}$ groups, which are saturated or unsaturated and linear or branched $C_1$ to $C_{22}$ hydrocarbon groups,
  a hydrogen atom,
$R_{45}$ is chosen from:
  the group

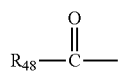

$R_{49}$ groups, which are saturated or unsaturated and linear or branched $C_1$ to $C_6$ hydrocarbon groups,
  a hydrogen atom,
$R_{44}$, $R_{46}$ and $R_{48}$, which may be identical or different, are chosen from linear or branched, saturated or unsaturated $C_7$ to $C_{21}$ hydrocarbon-based groups,
r, s and t, which are identical or different, are integers having values from 2 to 6;
y is an integer having a value from 1 to 10;
x and z, which may be identical or different, are integers ranging from 0 to 10;
X⁻ is a simple or complex and organic or inorganic anion;
with the proviso that the sum x+y+z is from 1 to 15, that when x is 0 then $R_{43}$ denotes $R_{47}$, and that when z is 0 then $R_{45}$ denotes $R_{49}$.

The alkyl groups $R_{42}$ may be linear or branched, and more particularly linear.

Preferably, $R_{42}$ denotes a methyl, ethyl, hydroxyethyl or dihydroxypropyl group and more particularly a methyl or ethyl group.

Advantageously, the sum x+y+z has a value from 1 to 10.

When $R_{43}$ is an $R_{47}$ hydrocarbon group, it can be long and have from 12 to 22 carbon atoms or be short and have from 1 to 3 carbon atoms.

When $R_{45}$ is an $R_{49}$ hydrocarbon group, it preferably has from 1 to 3 carbon atoms.

Advantageously, $R_{44}$, $R_{46}$ and $R_{48}$, which are identical or different, are chosen from linear or branched, saturated or unsaturated $C_{11}$ to $C_{21}$ hydrocarbon groups, and more particularly from linear or branched, saturated or unsaturated $C_{11}$ to $C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion X⁻ is preferably a halide (chloride, bromide or iodide) or an alkyl sulfate, more particularly methyl sulfate. However, it is possible to use methanesulfonate, phosphate, nitrate, tosylate, an anion derived from an organic acid, such as acetate or lactate, or any other anion that is compatible with the ammonium containing an ester function.

The anion X⁻ is even more particularly chloride or methyl sulfate.

Use is made more particularly in the composition according to the invention of the ammonium salts having formula (XV) in which:
$R_{42}$ denotes a methyl or ethyl group,
x and y are equal to 1;
z is equal to 0 or 1;
r, s and t are equal to 2;
$R_{43}$ is chosen from:
  the group

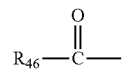

methyl, ethyl or $C_{14}$ to $C_{22}$ hydrocarbon-based groups,
  a hydrogen atom;

$R_{45}$ is chosen from:
the group

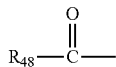

a hydrogen atom;
$R_{44}$, $R_{46}$ and $R_{48}$, which are identical or different, are chosen from saturated or unsaturated and linear or branched $C_{13}$ to $C_{17}$ hydrocarbon groups and preferably from saturated or unsaturated and linear or branched $C_{13}$ to $C_{17}$ alkyl and alkenyl groups.

Advantageously, the hydrocarbon-based groups are linear.

Examples that may be mentioned include the compounds having formula (XV) such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil, such as palm oil or sunflower oil. When the compound contains several acyl groups, they can be identical or different.

These products are obtained, for example, by direct esterification of triethanolamine, triisopropanolamine, alkyldiethanolamine or alkyldiisopropanolamine, which are optionally oxyalkylenated, with $C_{10}$ to $C_{30}$ fatty acids or with mixtures of $C_{10}$ to $C_{30}$ fatty acids of vegetable or animal origin, or by transesterification of their methyl esters. This esterification is followed by a quaternization using an alkylating agent such as an alkyl halide (preferably a methyl or ethyl halide), a dialkyl sulfate (preferably a dimethyl or diethyl sulfate), methyl methanesulfonate, methyl para-toluenesulfonate, glycol chlorohydrin or glycerol chlorohydrin.

Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention can contain, for example, a mixture of quaternary ammonium mono-, di- and triester salts with a predominance by weight of diester salts.

It is also possible to use the ammonium salts containing at least one ester function that are described in U.S. Pat. Nos. 4,874,554 and 4,137,180.

Use may be made of behenoylhydroxypropyltrimethylammonium chloride, provided by Kao under the name Quatarmin BTC 131.

Preferably, the ammonium salts comprising at least one ester functional group comprise two ester functional groups.

Among the quaternary ammonium salts containing at least one ester function which can be used, it is preferred to use dipalmitoylethylhydroxyethylmethylammonium salts.

The cationic surfactant(s) present in the composition according to the invention are more preferentially chosen from quaternary ammonium salts having formula (XII) described hereinbefore, the quaternary ammonium salts containing at least one ester function, and their mixtures.

More preferentially, the cationic surfactant(s) present in the composition according to the invention are chosen from cetyltrimethylammonium chloride, dipalmitoylethylhydroxyethylammonium methosulfate and their mixtures, and better cetyltrimethylammonium chloride.

The cationic surfactant(s) may be present in the composition according to the invention in a content ranging from 0.05% to 10% by weight, preferably from 0.1% to 5% by weight and more preferably ranging from 0.3% to 2% by weight relative to the total weight of the composition.

Fatty Substances

The composition according to the invention may optionally also comprise one or more fatty substances.

The term "fatty substance" means an organic compound that is insoluble in water at ordinary temperature (25° C.) and at atmospheric pressure (760 mmHg) (solubility of less than 5%, preferably less than 1% and even more preferentially less than 0.1%). They bear in their structure at least one hydrocarbon-based chain including at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Preferably, the fatty substances of the invention do not contain any salified or unsalified carboxylic acid groups (—C(O)OH or —C(O)O—). Particularly, the fatty substances of the invention are neither polyoxyalkylenated nor polyglycerolated.

Preferably, the fatty substances used in the composition according to the invention are non-silicone oils.

The term "oil" means a fatty substance that is liquid at room temperature (25° C.) and at atmospheric pressure (760 mmHg).

The term "non-silicone oil" means an oil not containing any silicon atoms (Si) and the term "silicone oil" means an oil containing at least one silicon atom.

More particularly, the fatty substance(s) are chosen from $C_6$ to $C_{16}$ hydrocarbons, hydrocarbons containing more than 16 carbon atoms, non-silicone oils of animal origin, plant oils of triglyceride type, synthetic triglycerides, fluoro oils, fatty alcohols, esters of fatty acids and/or of fatty alcohols other than triglycerides, and plant waxes, non-silicone waxes and silicones.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, which are optionally substituted, in particular, with one or more (in particular 1 to 4) hydroxyl groups. If they are unsaturated, these compounds may comprise one to three conjugated or unconjugated carbon-carbon double bonds.

As regards the $C_6$ to $C_{16}$ hydrocarbons, they are linear, branched or optionally cyclic, and are preferably alkanes. Examples that may be mentioned include hexane, dodecane and isoparaffins such as isohexadecane and isodecane.

A hydrocarbon-based oil of animal origin that may be mentioned is perhydrosqualene.

The triglyceride oils of plant or synthetic origin are preferably chosen from liquid fatty acid triglycerides containing from 6 to 30 carbon atoms, for instance heptanoic or octanoic acid triglycerides, or alternatively, for example, sunflower seed oil, corn oil, soybean oil, pumpkin oil, grapeseed oil, sesame seed oil, hazelnut oil, apricot oil, macadamia oil, arara oil, castor oil, avocado oil, tea seed oil, passion seed oil, meadowfoam seed oil, caprylic/capric acid triglycerides, for instance those sold by the company Stearineries Dubois or those sold under the names Miglyol® 810, 812 and 818 by the company Dynamit Nobel, jojoba oil and shea butter oil.

The linear or branched hydrocarbons of mineral or synthetic origin, containing more than 16 carbon atoms, are preferably chosen from liquid paraffins, petroleum jelly, liquid petroleum jelly, polydecenes and hydrogenated polyisobutene such as Parleam®.

The fluoro oils may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the composition according to the invention are saturated or unsaturated, and linear or branched, and include from 6 to 30 carbon atoms and more particularly from 8 to 18 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecyl-pentadecanol, oleyl alcohol and linoleyl alcohol.

The wax(es) that may be used in the composition according to the invention are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the fatty acid and/or fatty alcohol esters, which are advantageously different from the triglycerides mentioned above, mention may be made in particular of esters of saturated or unsaturated, linear or branched $C_1$ to $C_{26}$ aliphatic mono- or polyacids and of saturated or unsaturated, linear or branched $C_1$ to $C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$ to $C_{22}$ dicarboxylic or tricarboxylic acids and of $C_1$ to $C_{22}$ alcohols and esters of mono-, di- or tricarboxylic acids and of $C_2$ to $C_{26}$ di-, tri-, tetra- or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$ to $C_{30}$ and preferably $C_{12}$ to $C_{22}$ fatty acids. It is recalled that the term "sugar" means oxygenated hydrocarbon-based compounds that contain several alcohol functions, with or without aldehyde or ketone functions, and that include at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$ to $C_{30}$ and preferably $C_{12}$ to $C_{22}$ fatty acids. If they are unsaturated, these compounds may comprise one to three conjugated or unconjugated carbon-carbon double bonds.

The esters according to this alternative form can also be chosen from mono-, di-, tri- and tetraesters and polyesters, and mixtures thereof.

These esters may be, for example, oleates, laurates, palmitates, myristates, behenates, cocoates, stearates, linoleates, linolenates, caprates or arachidonates, or mixtures thereof such as, in particular, oleate/palmitate, oleate/stearate or palmitate/stearate mixed esters.

More particularly, use is made of mono- and diesters and in particular mono- or di-oleate, -stearate, -behenate, -oleate/palmitate, -linoleate, -linolenate or -oleate/stearate of sucrose, glucose or methylglucose.

Mention may be made, by way of example, of the product sold under the name Glucate® DO by the company Amerchol, which is a methylglucose dioleate.

Examples of esters or mixtures of sugar esters of fatty acid that may also be mentioned include:

the products sold as F160, F140, F110, F90, F70 and SL40 by Crodesta, respectively denoting sucrose palmitate/stearates formed of 73% monoester and 27% di- and triester, of 61% monoester and 39% di-, tri- and tetraester, of 52% monoester and 48% di-, tri- and tetraester, of 45% monoester and 55% di-, tri- and tetraester, and of 39% monoester and 61% di-, tri- and tetraester, and sucrose mono laurate;

the products sold as Ryoto Sugar Esters, for example referenced B370 and corresponding to sucrose behenate formed of 20% monoester and 80% diester, triester and polyester;

the sucrose mono-dipalmitate/stearate sold by the company Goldschmidt under the name Tegosoft® PSE.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes including at least one functional group chosen from amino groups, aryl groups and alkoxy groups.

Organopolysiloxanes are defined in greater detail in Walter Noll's "Chemistry and Technology of Silicones" (1968), Academic Press. They may be volatile or non-volatile.

When they are volatile, the silicones are more particularly chosen from those having a boiling point of between 60° C. and 260° C., and more particularly still from:

(I) cyclic polydialkylsiloxanes including from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, having formula:

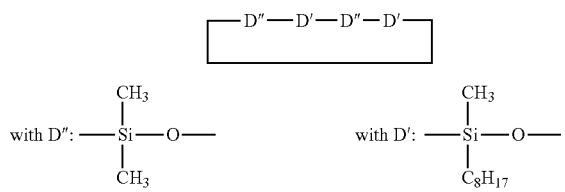

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5\times10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, "Volatile Silicone Fluids for Cosmetics".

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes bearing trimethylsilyl end groups. The viscosity of the silicones is measured at 25° C. according to Standard ASTM 445 Appendix C.

Among these polydialkylsiloxanes, mention may be made, in a nonlimiting manner, of the following commercial products:

the Silbione oils of the 47 and 70 047 series or the Mirasil oils sold by Rhodia, for instance the oil 70 047 V 500 000, the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes having dimethylsilanol end groups known as dimethiconol (CTFA), such as the oils in the 48 series from Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The silicone gums that can be used in accordance with the invention are in particular polydialkylsiloxanes and preferably polydimethylsiloxanes having high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:

the mixtures formed from a hydroxy-terminated polydimethylsiloxane or dimethiconol (CTFA), and from a cyclic polydimethylsiloxane, also known as cyclomethicone (CTFA), such as the product Q2 1401 sold by the company Dow Corning;

mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities, and more particularly of a PDMS gum and of a PDMS oil, such as the product SF 1236 from the company General Electric. The product SF 1236 is a mixture of a gum SE 30 defined above, with a viscosity of 20 m$^2$/s and of an oil SF 96 with a viscosity of $5\times10^{-6}$ m$^2$/s. This product preferably includes 15% of gum SE 30 and 85% of an oil SF 96.

The organopolysiloxane resins that may be used in accordance with the invention are crosslinked siloxane systems containing the following units:

$R_2SiO_{2/2}$, $R_3SiO_{1/2}$, $RSiO_{3/2}$ and $SiO_{4/2}$, in which R represents an alkyl containing 1 to 16 carbon atoms. Among these products, the ones that are particularly preferred are those in which R denotes a $C_1$-$C_4$ lower alkyl group, more particularly methyl.

Mention may be made, among these resins, of the product sold as Dow Corning 593 or those sold as Silicone Fluid SS 4230 and SS 4267 by General Electric, which are silicones having dimethyl/trimethylsiloxane structure.

Mention may also be made of the resins of the trimethylsiloxysilicate type, sold in particular as X22-4914, X21-5034 and X21-5037 by Shin-Etsu.

The organomodified silicones that may be used in accordance with the invention are silicones as defined previously and including in their structure one or more organofunctional groups attached via a hydrocarbon-based group.

The organomodified silicones may be polydiarylsiloxanes, in particular polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ m$^2$/s at 25° C.

Among these polyalkylarylsiloxanes, examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may also be made of polyorganosiloxanes including:

substituted or unsubstituted amino groups, such as the products sold under the names GP 4 Silicone Fluid and GP 7100 by the company Genesee or the products sold under the names Q2 8220 and Dow Corning 929 or 939 by the company Dow Corning. The substituted amino groups are, in particular, $C_1$-$C_4$ aminoalkyl groups;

alkoxylated groups, such as the product sold under the name Silicone Copolymer F-755 by SWS Silicones and Abil Wax® 2428, 2434 and 2440 by the company Goldschmidt.

Preferably, the fatty substances that may be used in the composition according to the invention are non-silicone fatty substances.

Preferably, the fatty substance(s) are chosen from fatty alcohols, fatty esters, oils of mineral origin, plant oils of triglyceride type and their mixtures.

The fatty substance(s), when they are present in the composition according to the invention, may be in content ranging from 1% to 30% by weight, preferably from 5% to 25% by weight and more preferably ranging from 10% to 20% by weight relative to the total weight of the composition.

Organic Acids

The composition may also comprise one or more organic acids.

For the purposes of the present invention, the term "organic acid" means an organic acid and/or the associated bases thereof with a pKa of less than or equal to 7, preferably less than or equal to 6, especially ranging from 1 to 6 and preferably from 2 to 5.

According to a preferred embodiment, the organic acid(s) are chosen from carboxylic acids, sulfonic acids and their mixtures.

Preferably, the organic acid(s) are chosen from saturated or unsaturated carboxylic acids.

Preferably, the organic acid(s) are preferably chosen from lactic acid, propanoic acid, butanoic acid, acetic acid, citric acid, maleic acid, glycolic acid, salicylic acid, malic acid, tartaric acid and their mixtures, and more preferably lactic acid.

The organic acids(s), when they are present in the composition according to the invention, may be in content ranging from 0.1% to 10% by weight, and preferably from 0.5% to 5% by weight relative to the total weight of the composition.

The term "cosmetically acceptable medium" means a medium that is compatible with keratin fibres, such as the hair.

The cosmetically acceptable medium is formed from water or from a mixture of water and one or more cosmetically acceptable solvents chosen from $C_1$-$C_4$ lower alcohols, such as ethanol, isopropanol, tert-butanol or n-butanol; polyols such as glycerol, propylene glycol and polyethylene glycols; and mixtures thereof.

The pH of the compositions according to the invention generally ranges from 3 to 10, preferably from 3 to 7, more preferentially from 4 to 7 and better still from 4 to 6.

The composition may also additionally comprise one or more additional additives.

The composition according to the invention may optionally comprise one or more additives, different from the compounds of the invention and among which mention may be in particular made of nonionic, zwitterionic or amphoteric surfactants, anionic, nonionic, amphoteric polymers or mixtures thereof, antidandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, especially polymeric thickeners, opacifiers or pearlizing agents, antioxidants, hydroxyacids, fragrances, preservatives, pigments and ceramides.

Needless to say, a person skilled in the art will take care to select this or these optional additional compound(s) such that the advantageous properties intrinsically associated with the composition according to the invention are not, or are not substantially, adversely affected by the envisaged addition(s).

The above adjuvants may generally be present in an amount comprised, for each of them, of between 0 and 20% by weight relative to the total weight of the ready-to-use composition.

The present invention also relates to a cosmetic keratin fibre treatment process, which consists in applying to said fibres an effective amount of a composition as described previously.

The composition may be applied to dry or damp keratin fibres that have previously optionally been washed with shampoo. Preferably, the composition according to the invention is applied to damp keratin fibres.

After the treatment, the keratin fibres are optionally rinsed with water, optionally washed with a shampoo and then rinsed with water, before being dried or left to dry.

The composition according to the present invention is applied with a leave-on time that may range from 1 to 15 minutes, preferably from 2 to 10 minutes.

The present invention finally relates to the use of a composition as described hereinbefore to give keratin fibres a cosmetic treatment that is long-lasting after being washed with shampoo.

According to the present application, "keratin fibres" means human keratin fibres and more specifically hair.

The examples that follow serve to illustrate the invention without, however, being limiting in nature.

EXAMPLES

In the examples that follow, all the amounts are given as percentages by weight relative to the total weight of the composition.

I. Example 1 a. Compositions Tested

The following compositions, A1 (invention) and B1 (comparison), have been prepared from ingredients whose contents are indicated in the table below.

|  | A1 (invention) | B1 (comparison) |
| --- | --- | --- |
| Cetylstearyl alcohol (50/50: $C_{16}/C_{18}$) | 9 | 9 |
| Mixture of myristyl stearate and myristyl palmitate | 1 | 1 |
| White mineral oil | 3 | 3 |
| Dipalmitoylethylhydroxyethylmethyl-ammonium methosulfate/cetearyl alcohol (30/70) | 4.5 (1.35 AI + 3.15 AI) | 4.5 (1.35 AI + 3.15 AI) |
| Cetyltrimethylammonium chloride (25% aqueous solution) | 3.2 (0.8 AI) | 3.2 (0.8 AI) |
| 3-Aminopropyltriethoxysilane | 5 | — |
| Lactic acid | 2 | 2 |
| Chlorhexidine digluconate | 0.1 | 0.1 |
| Preservative, Fragrance | qs | qs |
| Polydimethyldiallylammonium chloride (40% aqueous solution) | 1.2 (0.48 AI) | — |
| Water | qs 100 | qs 100 |
| pH | 5 ± 0.2 | 5 ± 0.2 |

AI: Active Ingredient

The resulting compositions A1 and B1 were applied to the same hair, by applying each composition to a half-head at 6 g per half head, on damp hair. The experiment was repeated on 14 models.

An expert then evaluated each of the following conditioning properties: detangling, suppleness, smoothness. The detangling was evaluated using a comb, whereas the other properties were scored on feel. For each of the 14 experiments, the expert attributed a score ranging from 0 to 5, where 0 corresponds to a minimum conditioning level and 5 corresponds to a maximum conditioning level.

Then the persistence of each of these properties after 3 washes with shampoo was evaluated according to the same criteria as previously.

b. Results

The results of the conditioning properties are given in the following table (average values for the 14 experiments).

|  |  | After application | After 3 washes with shampoo |
| --- | --- | --- | --- |
| Disentangling | A1 | 3.6 | 3.1 |
|  | B1 | 3.6 | 2.2 |
| Suppleness | A1 | 3.3 | 3.2 |
|  | B1 | 3.3 | 2.6 |
| Smoothness | A1 | 2.8 | 2.9 |
|  | B1 | 3.2 | 1.9 |

For smoothness, although the invention performs slightly less well than the comparison after application (at T0), it is observed that the effect is long-lasting after 3 washes with shampoo for the invention whereas it is not for the comparison.

The results above show that the hair treated with the composition according to the invention (A1) has good conditioning properties, that persist after washing with shampoo, by contrast with the conditioning effects obtained with the comparison composition (B1). Indeed, even after three washes, hair treated with the composition (A1) retain their conditioning properties. By contrast, the properties obtained with composition (B1) degrade.

II. Example 2 a. Compositions Tested

The following compositions, A2 (invention) and B2 (comparison), have been prepared from ingredients whose contents are indicated in the table below.

|  | A2 (invention) | B2 (comparison) |
| --- | --- | --- |
| Cetyltrimethylammonium chloride | 3.2% (0.8% AM) | 3.2% (0.8% AM) |
| 3-Aminopropyltriethoxysilane | 5% | 5% |
| Polyquaternium-6 (Charge density: 6 meq/g) | 1.2% (0.4% AI) | — |
| Polyquaternium-10 (Charge density: 1.1 meq/g) | — | 0.44% (0.4% AI) |
| Water | Qs 100% | Qs 100% |
| pH | 5 ± 0.2 | 5 ± 0.2 | b. Procedure

The resulting compositions A2 and B2 were applied at 1 g on tresses of bleached, damp hair weighing 2.7 g.

Using a comb, an expert then evaluated the persistence of detangling after 3 washes with shampoo, for each of the tresses tested, attributing scores ranging from 0 to 5, where 0 corresponds to minimum detangling (very difficult detangling) and 5 corresponds to a very easy level of detangling.

c. Results

The results of the detangling properties are given in the following table (average value for the 2 tresses).

|  | After 3 washes with shampoo |
| --- | --- |
| A2 (invention) | 5 |
| B2 (comparison) | 1 |

The results above show that the presence of a cationic polymer having charge density greater than or equal to 4 meq/g is necessary to produce good conditioning properties, which are long-lasting after 3 washes with shampoo. So hair treated with the composition comprising the Polyquaternium-6 (invention) detangles much better than hair treated with the composition comprising Polyquaternium-10 (comparison), after 3 washes with shampoo.

III. Example 3 a. Compositions Tested

The following compositions, A1 (invention) and B3 (comparison), have been prepared from ingredients whose contents are indicated in the table below.

|  | A1 (invention) | B3 (comparison) |
| --- | --- | --- |
| Cetylstearyl alcohol (50/50: $C_{16}/C_{18}$) | 9 | 9 |
| Mixture of myristyl stearate and myristyl palmitate | 1 | 1 |

-continued

|  | A1 (invention) | B3 (comparison) |
|---|---|---|
| White mineral oil | 3 | 3 |
| Dipalmitoylethylhydroxyethylmethyl-ammonium methosulfate/cetearyl alcohol (30/70) | 4.5 (1.35 AI + 3.15 AI) | 4.5 (1.35 AI + 3.15 AI) |
| Cetyltrimethylammonium chloride (25% aqueous solution) | 3.2 (0.8 AI) | 3.2 (0.8 AI) |
| 3-Aminopropyltriethoxysilane | 5 | 5 |
| Lactic acid | 2 | 2 |
| Chlorhexidine digluconate | 0.1 | 0.1 |
| Preservative, Fragrance | Qs | Qs |
| Polydimethyldiallylammonium chloride (40% aqueous solution) | 1.2 (0.48 AI) | — |
| Water | Qs 100 | Qs 100 |
| pH | 5 ± 0.2 | 5 ± 0.2 |

AI: active ingredient

The resulting compositions A1 and B3 have been applied at 6 g per half head on damp hair. The experiment was run on 6 models having sensitized hair.

Directly after compositions A1 and B3 were applied, using a comb an expert evaluated the level of detangling, for all of the 6 comparison experiments, by attributing scores ranging from 0 to 5, where 0 corresponds to minimum detangling (very difficult detangling) and 5 corresponds to a very easy level of detangling.

The persistence of detangling after 3 washes with shampoo was also determined, using the same criteria as previously.

b. Results

The results of the detangling properties are given in the following table (average value for the 6 experiments).

|  | After application | After 3 washes with shampoo |
|---|---|---|
| A1 (invention) | 3.6 | 3.4 |
| B3 (comparison) | 3.8 | 2.8 |

The results above show that the composition according to the present invention (A1) can produce good detangling properties.

Moreover, in contrast to the properties produced with composition B3, those obtained with composition A1 are long-lasting when washed with shampoo. So even after three washes with shampoo, the hair treated with the composition comprising a cationic polymer having charge density equal to 4 meq/g (invention) retains its detangling properties. By contrast, these properties fade when hair is treated with a composition that does not comprise a cationic polymer having charge density greater than or equal to 4 meq.

The presence of this specific type of cationic polymer is therefore necessary to secure a long-lasting effect for the cosmetic properties.

IV. Example 4 a. Compositions Tested

The following compositions, A1 (invention) and B4 (comparison), have been prepared from ingredients whose contents are indicated in the table below.

|  | A1 (invention) | B4 (comparison) |
|---|---|---|
| Cetylstearyl alcohol (50/50: $C_{16}/C_{18}$) | 9 | 9 |
| Mixture of myristyl stearate and myristyl palmitate | 1 | 1 |
| White mineral oil | 3 | 3 |
| Dipalmitoylethylhydroxyethylmethyl-ammonium methosulfate/cetearyl alcohol (30/70) | 4.5 (1.35 AI + 3.15 AI) | 4.5 (1.35 AI + 3.15 AI) |
| Cetyltrimethylammonium chloride (25% aqueous solution) | 3.2 (0.8 AI) | 3.2 (0.8 AI) |
| 3-Aminopropyltriethoxysilane | 5 | — |
| Lactic acid | 2 | 2 |
| Chlorhexidine digluconate | 0.1 | 0.1 |
| Preservative, Fragrance | Qs | Qs |
| Polydimethyldiallylammonium chloride (40% aqueous solution) | 1.2 (0.48 AI) | 1.2 (0.48 AI) |
| Water | Qs 100 | Qs 100 |
| pH | 5 ± 0.2 | 5 ± 0.2 |

AI: active ingredient

Compositions A1 and B4 have been applied at 6 g per half head on damp hair. The experiment was run on 6 models having sensitized hair.

Directly after compositions A1 and B4 were applied, using a comb an expert evaluated the level of detangling, for all of the 6 comparison experiments, by attributing scores ranging from 0 to 5, where 0 corresponds to minimum detangling (very difficult detangling) and 5 corresponds to a very easy level of detangling.

The persistence of detangling after 3 washes with shampoo was also determined, using the same criteria as previously.

b. Results

The results of the detangling properties are given in the following table (average value for the 6 experiments).

|  | After application | After 3 washes with shampoo |
|---|---|---|
| A1 (invention) | 3.2 | 3.3 |
| B4 (comparison) | 3.5 | 2.6 |

The results above show that the composition according to the present invention (A1) can produce detangling properties that are long-lasting for at least 3 washes with shampoo, in contrast with the properties obtained with composition B4. Indeed, after three washes, hair treated with the composition comprising 3-aminopropyltriethoxysilane (invention) retains its detangling properties. By contrast, these properties fade when hair is treated with a composition not comprising an organosilane having formula (I).

The presence of a silane having formula (I) is therefore necessary to secure a long-lasting effect for the cosmetic properties.

The invention claimed is:

1. A cosmetic composition for caring for keratin fibers, comprising, in a cosmetically acceptable medium:
   (i) one or more organosilanes chosen from 3-aminopropyltriethoxysilane, oligomers thereof, or mixtures thereof;
   (ii) one or more cationic polymers having a charge density greater than or equal to 4 meq/g chosen from:
      (1) alkyldiallylamine or dialkyldiallylammonium cyclopolymers;
      (2) crosslinked polymers of methacryloyloxyalkyl($C_1$-$C_4$) trialkyl($C_1$-$C_4$) ammonium salts; or (3) mixtures thereof, and
(iii) one or more cationic surfactants chosen from:
(a) quaternary ammonium salts of formula (XII) below:

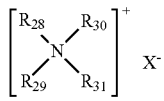
(XII)

in which,
R$_{28}$ to R$_{31}$, which can be identical or different, represent a linear or branched aliphatic group including from 1 to 30 carbon atoms or an aromatic group, at least one of the R$_{28}$ to R$_{31}$ groups denoting a group including from 8 to 30 carbon atoms, and
X$^-$ is an anion chosen from the group of halides, phosphates, acetates, lactates, (C$_1$-C$_4$)alkylsulfates, (C$_1$-C$_4$)alkylsulfonates and (C$_1$-C$_4$)alkyl-arylsulfonates,
(b) quaternary ammonium salts containing at least one ester function, or
(c) mixtures thereof;
wherein the pH of said composition ranges from 3 to 7,
wherein the amount of the organosilane(s) ranges from 1% to 8% by weight, relative to the total weight of the composition, and
the amount of cationic polymer(s) ranges from 0.1% to 15% by weight, relative to the total weight of the composition.

2. The composition according to claim 1, wherein the cationic polymer(s) are chosen from 2-methacryloyloxyethyl trimethyl ammonium chloride, dimethyldiallylammonium chloride or mixtures thereof.

3. The composition according to claim 1, wherein the cationic surfactant(s) are chosen from cetyltrimethylammonium chloride, dipalmitoylethylhydroxyethylammonium methosulfate or mixtures thereof.

4. The composition according to claim 1, wherein the content of cationic surfactant(s) ranges from 0.05% to 10% by weight, relative to the total weight of the composition.

5. The composition according to claim 1, further comprising one or more fatty substances.

6. The composition according to claim 5, wherein the content of the fatty substance(s) ranges from 1% to 30% by weight, relative to the total weight of the composition.

7. A method for the cosmetic treatment of keratin fibers, which consists in applying to the said keratin fibers a composition comprising, in a cosmetically acceptable medium:
(i) one or more organosilanes chosen from 3-aminopropyltriethoxysilane, oligomers thereof, or mixtures thereof;
(ii) one or more cationic polymers having a charge density greater than or equal to 4 meq/g chosen from
(1) alkyldiallylamine or dialkyldiallylammonium cyclopolymers;
(2) crosslinked polymers of methacryloyloxyalkyl(C$_1$-C$_4$) trialkyl(C$_1$-C$_4$) ammonium salts; or
(3) mixtures thereof, and
(iii) one or more cationic surfactants chosen from:
(a) quaternary ammonium salts of formula (XII) below:

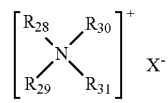
(XII)

in which,
R$_{28}$ to R$_{31}$, which can be identical or different, represent a linear or branched aliphatic group including from 1 to 30 carbon atoms or an aromatic group, at least one of the R$_{28}$ to R$_{31}$ groups denoting a group including from 8 to 30 carbon atoms, and
X$^-$ is an anion chosen from the group of halides, phosphates, acetates, lactates, (C$_1$-C$_4$)alkylsulfates, (C$_1$-C$_4$)alkylsulfonates and (C$_1$-C$_4$)alkyl-arylsulfonates,
(b) quaternary ammonium salts containing at least one ester function, or
(c) mixtures thereof;
wherein the pH of said composition ranges from 3 to 7,
wherein the amount of the organosilane(s) ranges from 0.1% to 8% by weight, relative to the total weight of the composition, and
and wherein the amount of cationic polymer(s) ranges from 1% to 15% by weight, relative to the total weight of the composition.

* * * * *